US007262542B2

(12) United States Patent
Toda

(10) Patent No.: US 7,262,542 B2
(45) Date of Patent: Aug. 28, 2007

(54) ULTRASOUND RADIATION DEVICE INTO A MATERIAL

(76) Inventor: Kohji Toda, 1-49-18 Futaba, Yokosuka (JP) 239-0814

( * ) Notice: Subject to any disclaimer, the term of this patent is extended or adjusted under 35 U.S.C. 154(b) by 39 days.

(21) Appl. No.: 11/267,602

(22) Filed: Nov. 7, 2005

(65) Prior Publication Data

US 2007/0103031 A1    May 10, 2007

(51) Int. Cl.
*H03H 9/25* (2006.01)
(52) U.S. Cl. .............................. 310/313 B; 310/313 R; 600/459; 367/140; 367/157; 367/164
(58) Field of Classification Search ................ 367/140, 367/157, 164; 600/459; 310/322, 334, 313 B, 310/313 R
See application file for complete search history.

(56) References Cited

U.S. PATENT DOCUMENTS 3,950,713 A * 4/1976 Lewis ........................ 333/151
6,317,389 B1   11/2001 Toda
6,360,611 B1 *  3/2002 Toda ............................ 73/651
6,522,047 B1 *  2/2003 Toda ..................... 310/313 B

* cited by examiner

Primary Examiner—Thomas M. Dougherty

(57) ABSTRACT

When input electric signals $E_i$ (i=1, 2, ..., n) with frequencies $f_i$ (i=1, 2, ..., n), respectively, are applied to an input interdigital transducer, elastic waves are excited in a piezoelectric substrate. Leaky components of the elastic waves are radiated into a material in the form of longitudinal waves, which are reflected at a bottom boundary-surface of the material. One of reflected longitudinal waves are detected at an output interdigital transducer as a delayed output signal with one of the frequencies $f_i$. When the delayed output signal is applied to at least one interdigital transducer for radiation, an elastic wave is excited in the piezoelectric substrate. A leaky component of the elastic wave is radiated into the material in the form of a longitudinal wave, which is reflected at the bottom boundary-surface and re-reflected at a top boundary-surface of the material, and thus a continuous reflection occurs.

19 Claims, 13 Drawing Sheets

ULTRASOUND RADIATION DEVICE INTO A MATERIAL

BACKGROUND OF THE INVENTION

The present invention relates to a device for radiating an ultrasound into a material by means of using an assembly composed of a piezoelectric substrate, input- and output interdigital transducers for delay-line oscillation, and another at least one interdigital transducer for ultrasound radiation into a material.

Popularly, a thickness mode piezoelectric transducer, of which operation frequency is dependent on the thickness of a piezoelectric substrate, is used for emitting an acoustic wave. However, such a conventional type of transducer has a difficulty in oblique incidence of the ultrasound into a liquid.

When the piezoelectric substrate is in contact with a liquid, an interdigital transducer (IDT) on the piezoelectric substrate is useful. By use of the IDT on the piezoelectric substrate, sufficiently thicker compared with the wavelength of a surface acoustic wave (SAW) thereon, the SAW propagates in the form of a leaky wave that is mode-converted to a longitudinal wave into the liquid. In this way, the IDT operates at a liquid-solid boundary as a leaky-wave transducer for bulk wave radiation into the liquid. However, the leaky SAW traveling on a sufficiently thick substrate compared with the wavelength has only one mode without velocity dispersion. Thus, a conventional transducer such as the IDT for the leaky SAW has a problem of a limited ultrasound-radiation angle.

An ultrasound-signal radiating device (U.S. Pat. No. 6,317,389) and a device for ultrasound radiation into a material (U.S. Pat. No. 6,360,611) were provided in order to enable a multi-modes operation at a high frequency. These conventional devices, suitable for radiating an ultrasound into a material, for example, a cellular tissue, are excellent in adjusting of radiation angle and sweeping of ultrasound beam. However, these conventional devices have a difficulty in radiation of ultrasound beam reaching the bottom of a material with a high efficiency. In addition, these conventional devices have a difficulty in continuous driving at a suitable frequency while moving itself on a surface of a material, of which the depth changes.

BRIEF SUMMARY OF THE INVENTION

An object of the present invention is to provide an ultrasound radiation device into a material capable of changing the driving frequency in response to the depth of the material.

Another object of the present invention is to provide an ultrasound radiation device into a material capable of a high efficiency operation under low electric power consumption.

Another object of the present invention is to provide an ultrasound radiation device into a material capable of radiating an ultrasound into a cellular tissue.

Another object of the present invention is to provide an ultrasound radiation device into a material capable of radiating a message-signal, for example, a music, into a material.

Another object of the present invention is to provide an ultrasound radiation device into a material excellent in durability and manufacturing.

Another object of the present invention is to provide an ultrasound radiation device into a material not affected by a change in circumstances, for example, a change in temperature.

A still other object of the present invention is to provide an ultrasound radiation device into a material easy in use and having a small size which is very light in weight and has a simple structure.

According to one aspect of the present invention there is provided an ultrasound radiation device into a material comprising a piezoelectric substrate, input and output interdigital transducers, another at least one interdigital transducer for radiation, and an amplifier. When input electric signals $E_i$ (i=1, 2, . . . , n) with frequencies $f_i$ (i=1, 2, . . . , n), respectively, are applied to the input interdigital transducer receiving at a time, elastic waves are excited in the piezoelectric substrate. Leaky components of the elastic waves are radiated into a material in the form of longitudinal waves, and reflected at a bottom boundary-surface of the material. Then, one of reflected longitudinal waves is detected at the output interdigital transducer as a delayed output signal, which has one of the frequencies $f_i$ in accordance with a distance between the bottom boundary-surface and a top boundary-surface of the material. The delayed output signal is amplified via the amplifier. A signal part of an amplified electric signal is fed back to the input interdigital transducer as an input electric signal, again. Thus, a self-oscillation type of delay-line oscillator operating at the one of the frequencies $f_i$ occurs. When a remaining signal part of the amplified electric signal is applied to the interdigital transducer for radiation, an elastic wave is excited in the piezoelectric substrate. A leaky component of the elastic wave is radiated into the material in the form of a longitudinal wave, and reflected at the bottom boundary-surface, and then, re-reflected at the top boundary-surface of the material. Thus, a continuous reflection as a chain reaction occurs.

According to another aspect of the present invention there is provided an ultrasound radiation device into a material further comprising a polymer film, with which a downward surface of the piezoelectric substrate is coated.

According to another aspect of the present invention there is provided a piezoelectric substrate having a hole between the input- and output interdigital transducers formed on a central surface-part of an upward surface of the piezoelectric substrate.

According to another aspect of the present invention there is provided a piezoelectric substrate having an intercepting material between the input- and output interdigital transducers on the central surface-part.

According to another aspect of the present invention there is provided a piezoelectric substrate having an intercepting material, with conductivity, between the input- and output interdigital transducers on the central surface-part.

According to another aspect of the present invention there is provided a piezoelectric substrate made of a piezoelectric ceramic thin plate, the polarization axis thereof being parallel to the thickness direction thereof.

According to another aspect of the present invention there is provided a piezoelectric substrate made of a piezoelectric polymer thin film.

According to another aspect of the present invention there is provided input- and output interdigital transducers having normal interdigital electrode-patterns, respectively.

According to another aspect of the present invention there is provided another at least one interdigital transducer having normal interdigital electrode-pattern.

According to another aspect of the present invention there is provided input- and output interdigital transducers and another at least one interdigital transducer for radiation having normal interdigital electrode-patterns, respectively. The electrode-finger length of the interdigital transducer for radiation is longer than the electrode-finger lengths of the input- and output interdigital transducers.

According to another aspect of the present invention there is provided input- and output interdigital transducers and another at least one interdigital transducer for radiation having normal interdigital electrode-patterns, respectively. The electrode-finger direction of the interdigital transducer for radiation is oblique to the electrode-finger directions of the input- and output interdigital transducers.

According to another aspect of the present invention there is provided input- and output interdigital transducers having arch-shaped electrode-patterns, respectively.

According to another aspect of the present invention there is provided another at least one interdigital transducer having an arch-shaped electrode-pattern.

According to another aspect of the present invention there is provided another at least one interdigital transducer having an arch-shaped electrode-pattern arranged so that the aperture thereof is faced to the center of the upward surface.

According to another aspect of the present invention there is provided another at least one interdigital transducer having an arch-shaped electrode-pattern arranged so that the aperture thereof is faced with its back to the center of the upward surface.

According to another aspect of the present invention there is provided input- and output interdigital transducers and another at least one interdigital transducer having dispersive electrode-patterns, respectively, of which each has a series of interdigital periodicities.

According to another aspect of the present invention there is provided input- and output interdigital transducers and another at least one interdigital transducer having dispersive electrode-patterns, respectively, of which each has a series of interdigital periodicities. The input- and output interdigital transducers are arranged so that one end electrode-finger participating the largest interdigital periodicity among the interdigital periodicities in the input interdigital transducer is close to that in the output interdigital transducer.

According to another aspect of the present invention there is provided an ultrasound radiation device into a material further comprising a modulator. When an input message-signal and the remaining signal part as a carrier signal are applied to the modulator, an amplitude of the carrier signal is modulated according to the input message-signal, and an amplitude-modulated signal is generated. The amplitude-modulated signal is applied to the interdigital transducer for radiation.

According to a further aspect of the present invention there is provided another at least two interdigital transducers mutually balanced for the center of the upward surface.

BRIEF DESCRIPTION OF THE SEVERAL VIEWS OF THE DRAWINGS

Other features and advantages of the invention will be clarified from the following description with reference to the attached drawings.

DETAILED DESCRIPTION OF THE INVENTION

Figure 1:
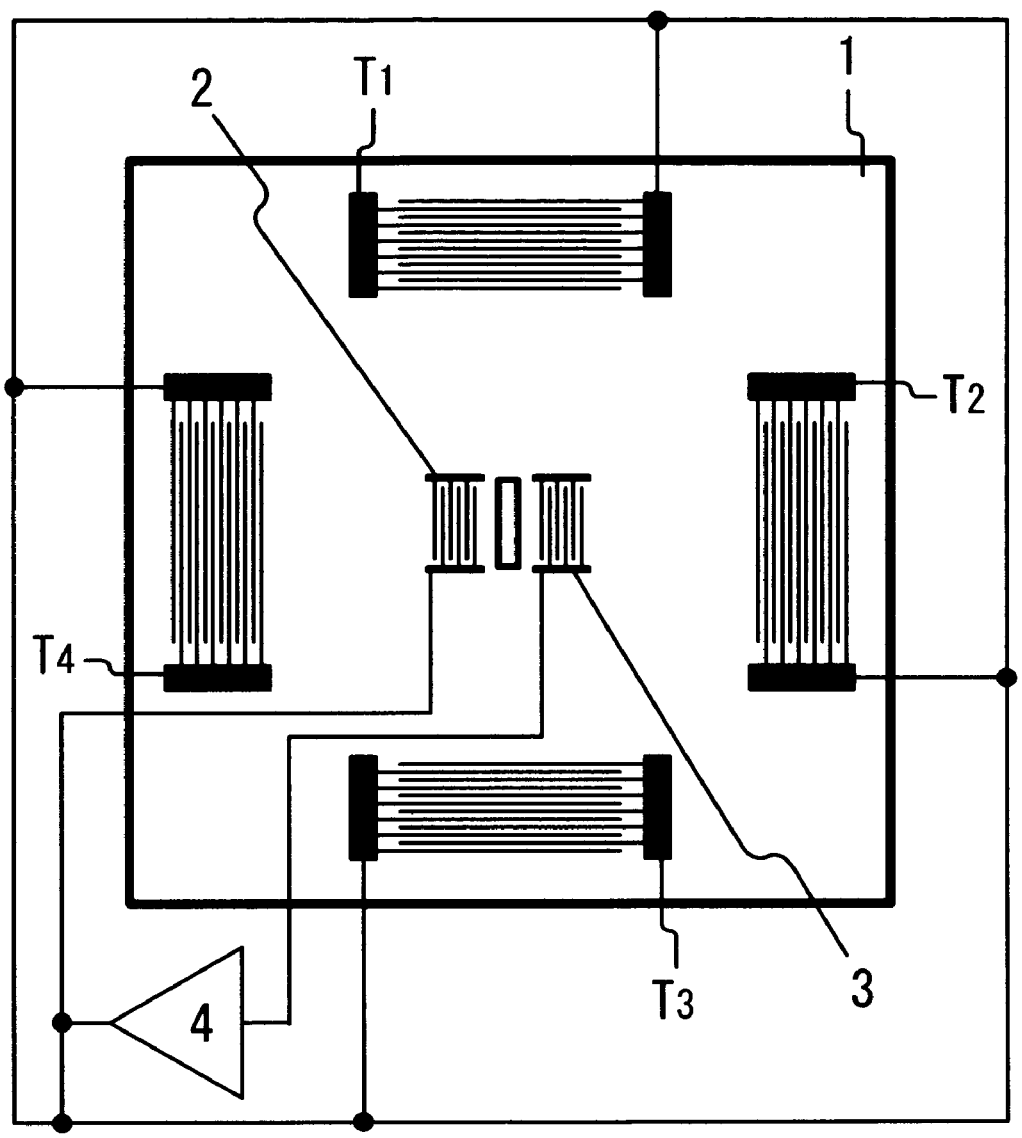
FIG. 1 shows a top plan view of an ultrasound radiation device into a material according to a first embodiment of the present invention.

FIG. 1 shows a top plan view of an ultrasound radiation device into a material according to a first embodiment of the present invention. The ultrasound radiation device into a material comprises piezoelectric substrate 1, input interdigital transducer 2, output interdigital transducer 3, four interdigital transducers ($T_1$, $T_2$, $T_3$ and $T_4$), amplifier 4, and polymer film 5 as silicone rubber, which is not drawn in FIG. 1. Though four interdigital transducers ($T_1$, $T_2$, $T_3$ and $T_4$) are used, only one interdigital transducer ($T_1$, $T_2$, $T_3$ or $T_4$) can be used in FIG. 1. Input interdigital transducer 2 and output interdigital transducer 3, having normal interdigital electrode-patterns made of aluminum thin films, respectively, are formed on a central surface-part of an upward surface of piezoelectric substrate 1. Interdigital transducers ($T_1$, $T_2$, $T_3$ and $T_4$) having normal interdigital electrode-patterns made of aluminum thin films, respectively, are formed on a surrounding surface-part of the upward surface of piezoelectric substrate 1. The electrode-finger lengths of interdigital transducers ($T_1$, $T_2$, $T_3$ and $T_4$) are longer than those of input interdigital transducer 2 and output interdigital transducer 3. The electrode-finger directions of interdigital transducers ($T_1$ and $T_3$) are orthogonal to those of input interdigital transducer 2 and output interdigital transducer 3. On the other hand, the electrode-finger directions of interdigital transducers ($T_2$ and $T_4$) are parallel to those of input interdigital transducer 2 and output interdigital transducer 3. In this way, interdigital transducers ($T_1$, $T_2$, $T_3$ and $T_4$) are mutually balanced for the center of the upward surface.

Figure 2:
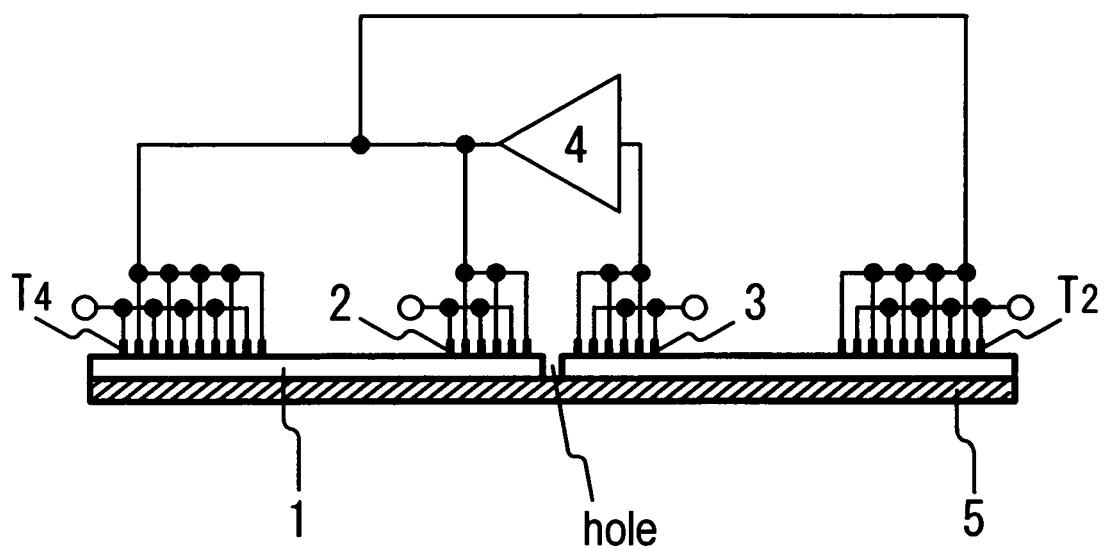
FIG. 2 shows a sectional view of the ultrasound radiation device into a material in FIG. 1.

FIG. 2 shows a sectional view of the ultrasound radiation device into a material in FIG. 1. Interdigital transducers ($T_1$ and $T_3$) and amplifier 4 are not drawn in FIG. 2. Piezoelectric substrate 1 is made of a piezoelectric ceramic thin plate with a dimension of 220 μm in thickness, and has a hole between input interdigital transducer 2 and output interdigital transducer 3. A downward surface of piezoelectric substrate 1 is covered with polymer film 5. It is possible to use a piezoelectric polymer thin film in place of piezoelectric substrate 1. Input interdigital transducer 2, output interdigital transducer 3, and interdigital transducers ($T_1$, $T_2$, $T_3$ and $T_4$) have an interdigital periodicity of 340 μm, respectively. Thus, the device for ultrasound radiation into a material in FIG. 1 has a small size which is very light in weight and has a simple structure.

In the ultrasound radiation device into a material in FIG. 1, if input electric signals $E_i$ (i=1, 2, ..., n) with frequencies $f_i$ (i=1, 2, ..., n), respectively, are applied to input interdigital transducer 2, elastic waves corresponding to the input electric signals $E_i$ are excited in piezoelectric substrate 1 efficiently, because piezoelectric substrate 1 is made of a piezoelectric ceramic, and in addition, the polarization axis thereof is parallel to the thickness direction thereof. Each elastic wave in piezoelectric substrate 1 is composed of a leaky component and a non-leaky component, which is not transmitted to output interdigital transducer 3 because of the hole between input interdigital transducer 2 and output interdigital transducer 3. The hole plays the role to intercept a transmission of the non-leaky component. Therefore, it is also possible that piezoelectric substrate 1 has an intercepting material such as conductive paint instead of the hole. Epoxy resin is also useful as the intercepting material.

Figure 3:
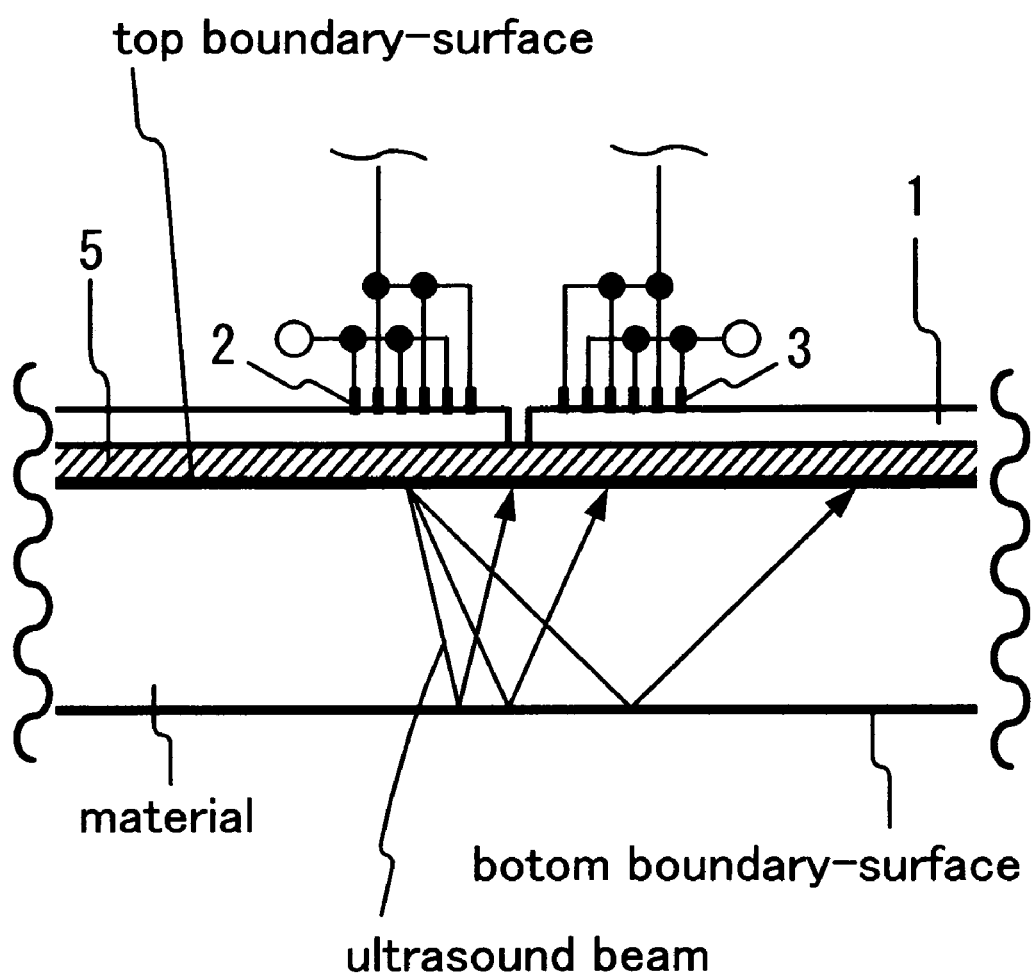
FIG. 3 shows a fragmentary sectional view of the ultrasound radiation device into a material in FIG. 1.

FIG. 3 shows a fragmentary sectional view of the ultrasound radiation device into a material in FIG. 1. Leaky components of the elastic waves excited in piezoelectric substrate 1 are radiated in the form of longitudinal waves into a material, for example, a cellular tissue, kept in contact with polymer film 5 on the downward surface of piezoelectric substrate 1. The use of polymer film 5 makes it possible to radiate the longitudinal waves into the material having a top boundary-surface and a bottom boundary-surface with a high efficiency. The longitudinal waves in a cellular tissue are reflected at the bottom boundary-surface between the material and another material, for example, bone, tooth and air. In this time, the longitudinal waves have radiation angles in response to the frequencies $f_i$ of the input electric signals $E_i$, respectively, so that reflected longitudinal waves at the bottom boundary-surface have various reflection angles according to the radiation angles of the longitudinal waves, respectively. Three arrows traced in FIG. 3 are illustrative of ultrasound beams in the material such as cellular tissue. One of the reflected longitudinal waves can be detected at output interdigital transducer 3 as a delayed output signal with one of the frequencies $f_i$.

In the ultrasound radiation device into a material in FIG. 1, the delayed output signal detected at output interdigital transducer 3 is amplified via amplifier 4. A signal part of an amplified electric signal via amplifier 4 is fed back to input interdigital transducer 2 as an input electric signal, again. Thus, input interdigital transducer 2, output interdigital transducer 3, and amplifier 4 form a self-oscillation type of delay-line oscillator operating at the one of the frequencies $f_i$. Such a self-oscillation type of delay-line oscillator provides a small-sized circuit, and enables a high efficiency operation under low electric power consumption, and then, makes the device not affected by a change in circumstances, for example, a change in temperature. On the other hand, a remaining signal part of the amplified electric signal via amplifier 4 is applied to interdigital transducers ($T_1$, $T_2$, $T_3$ and $T_4$). As a result, four elastic waves, of which each is composed of leaky- and non-leaky components, are excited in piezoelectric substrate 1.

Figure 4:
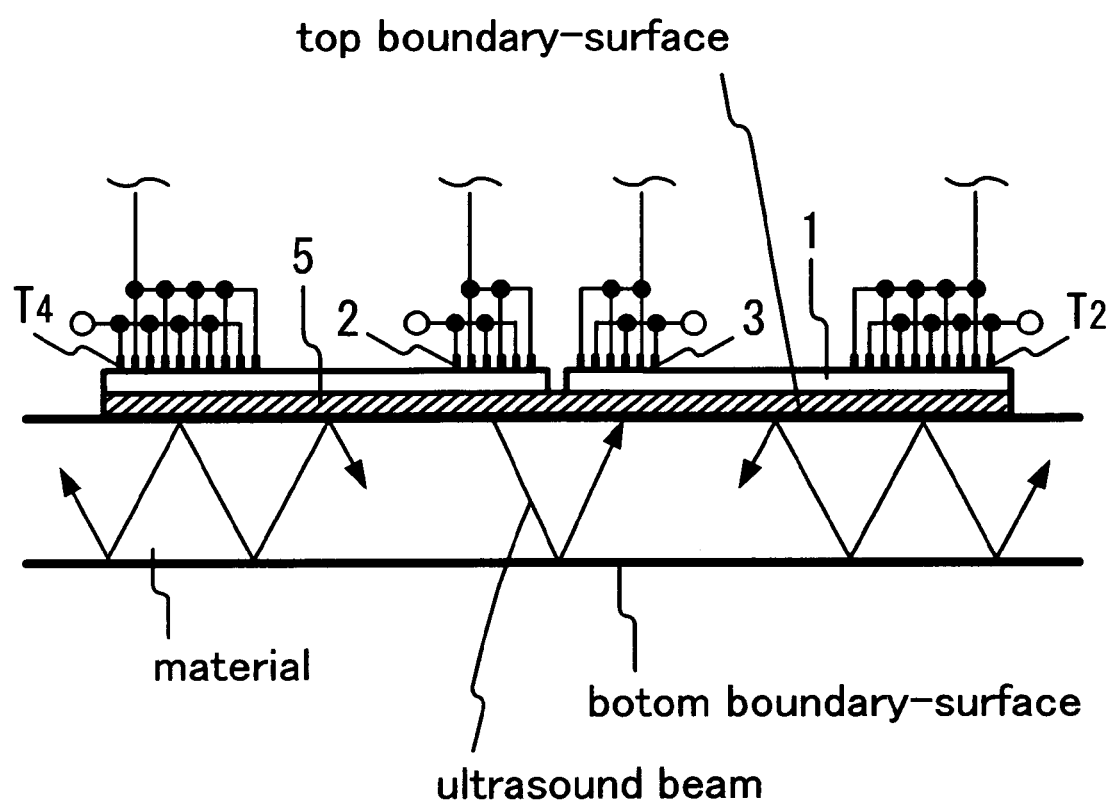
FIG. 4 shows another fragmentary sectional view of the ultrasound radiation device into a material in FIG. 1.

FIG. 4 shows another fragmentary sectional view of the ultrasound radiation device into a material in FIG. 1. The leaky component of each of the four elastic waves corresponding to interdigital transducers ($T_1$, $T_2$, $T_3$ and $T_4$) is radiated effectively in the form of a longitudinal wave into the material. The longitudinal wave is reflected at the bottom boundary-surface, and then re-reflected at the top boundary-surface, and thus, a continuous reflection as a chain reaction occurs. The continuous reflection causes the material filled with the ultrasound energy.

Figure 5:
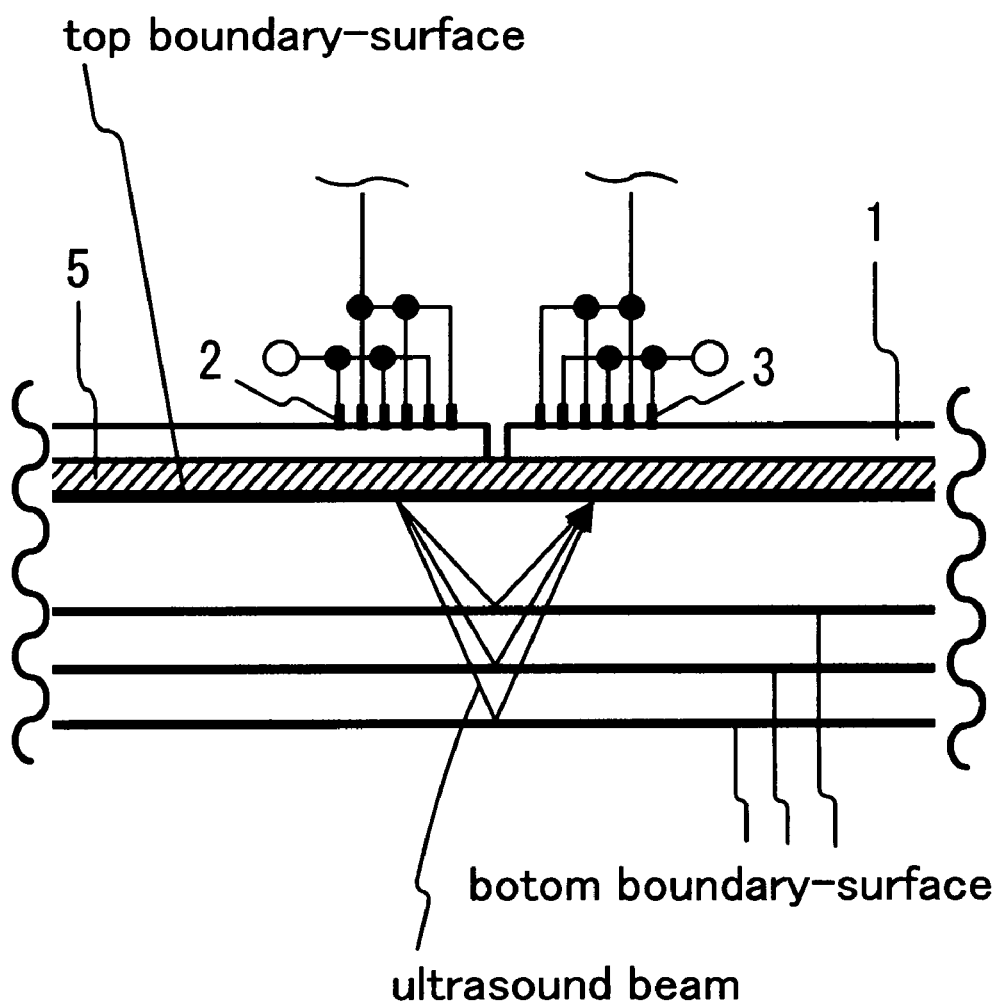
FIG. 5 shows a still other fragmentary sectional view of the ultrasound radiation device into a material in FIG. 1.

FIG. 5 shows a still other fragmentary sectional view of the ultrasound radiation device into a material in FIG. 1. As mentioned above, the longitudinal waves from input interdigital transducer 2 are reflected at one bottom boundary-surface shown in FIG. 3, and one of the reflected longitudinal waves can be detected at output interdigital transducer 3 as a delayed output signal. In other words, the reflected longitudinal wave detected at output interdigital transducer 3 has the reflection angle in response to the distance between the bottom boundary-surface and the top boundary-surface. Three arrows traced in FIG. 5 are illustrative of ultrasound beams in response to three bottom boundary-surfaces, respectively. It should be noticed that one reflected longitudinal wave is always detected at output interdigital transducer 3, even if the distance between the bottom boundary-surface and the top boundary-surface changes. After all, one of the reflected longitudinal waves in response to the frequencies $f_i$ of the input electric signals $E_i$, respectively, is certainly detected at output interdigital transducer 3 regardless of the depth of the material. In other words, it is possible for the ultrasound radiation device into a material to change the driving frequency and the radiation angle in response to the depth of the material, thus, to continue its driving at a suitable frequency while moving itself on a surface of the material, of which the depth changes, for example, moving on a skin where the depth of the cellular tissue changes.

As mentioned above, the ultrasound radiation device into a material in FIG. 1 enables effective radiation of the longitudinal waves into a cellular tissue regardless of the depth of the cellular tissue. Thus, the device in FIG. 1 is very useful for quickening the circulation of the blood and massage of skin, especially, at head, face, gums, and so on. In addition, the device in FIG. 1 is applied to hydroponics, that is, useful for germination and promotion of plant.

Figure 6:
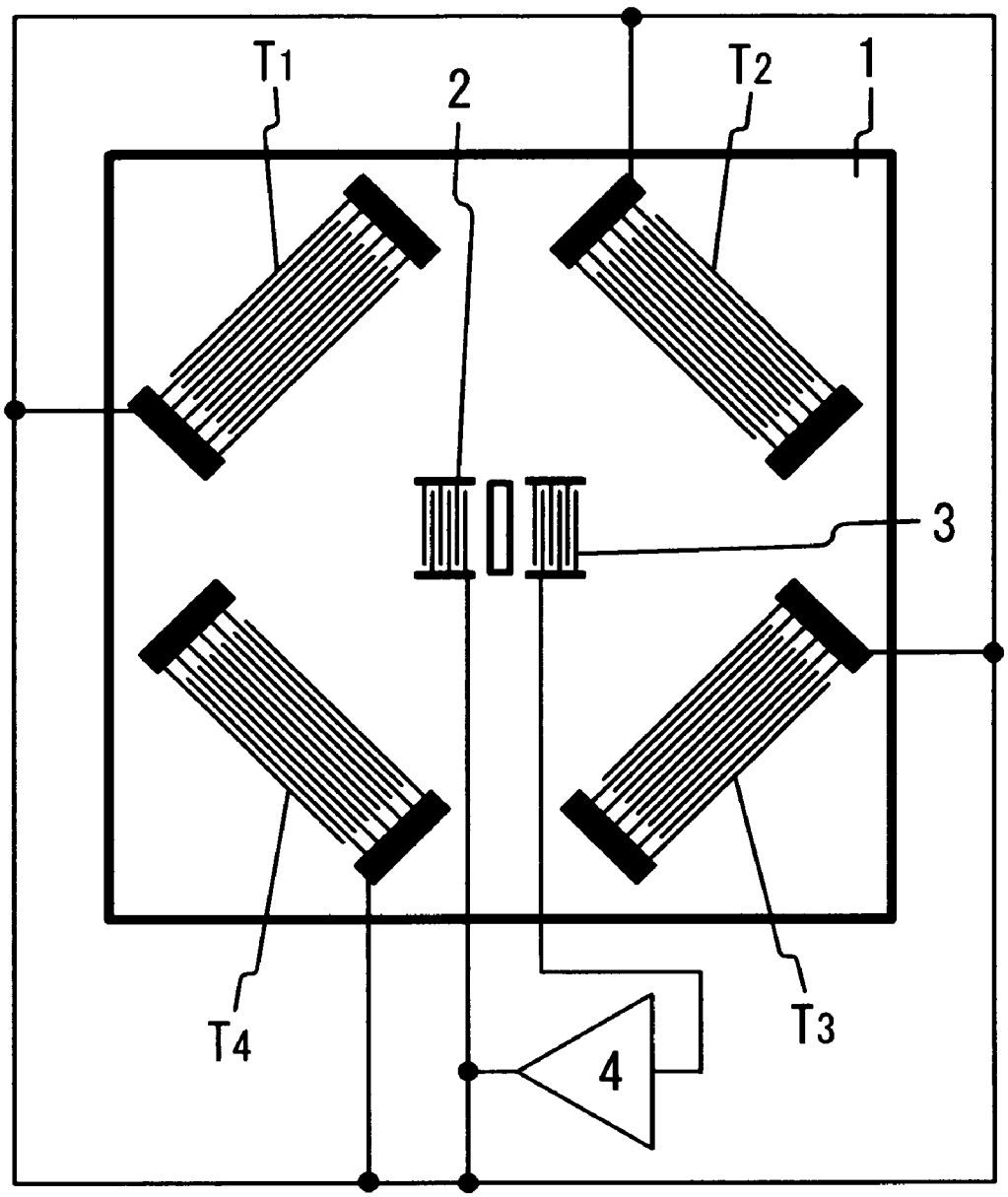
FIG. 6 shows a top plan view of an ultrasound radiation device into a material according to a second embodiment of the present invention.

FIG. 6 shows a top plan view of an ultrasound radiation device into a material according to a second embodiment of the present invention. The ultrasound radiation device into a material has the same construction as FIG. 1, except for the location of interdigital transducers ($T_1$, $T_2$, $T_3$ and $T_4$). The electrode-finger directions of interdigital transducers ($T_1$, $T_2$, $T_3$ and $T_4$) are oblique to those of input interdigital transducer 2 and output interdigital transducer 3. Interdigital transducers ($T_1$, $T_2$, $T_3$ and $T_4$) are mutually balanced for the center of the upward surface.

In the ultrasound radiation device into a material in FIG. 6, the radiation directions of the longitudinal waves from interdigital transducers ($T_1$, $T_2$, $T_3$ and $T_4$) are different from those of the longitudinal waves from input interdigital transducer 2 without exception. On the other hand, the radiation directions of the longitudinal waves from interdigital transducers ($T_1$, $T_2$, $T_3$ and $T_4$) are not always different from those of the longitudinal waves from input interdigital transducer 2 in FIG. 1. As a result, a noiseless and clear delayed output signal is detected at output interdigital transducer 3 in FIG. 6 in comparison with the ultrasound radiation device into a material in FIG. 1.

Figure 7:
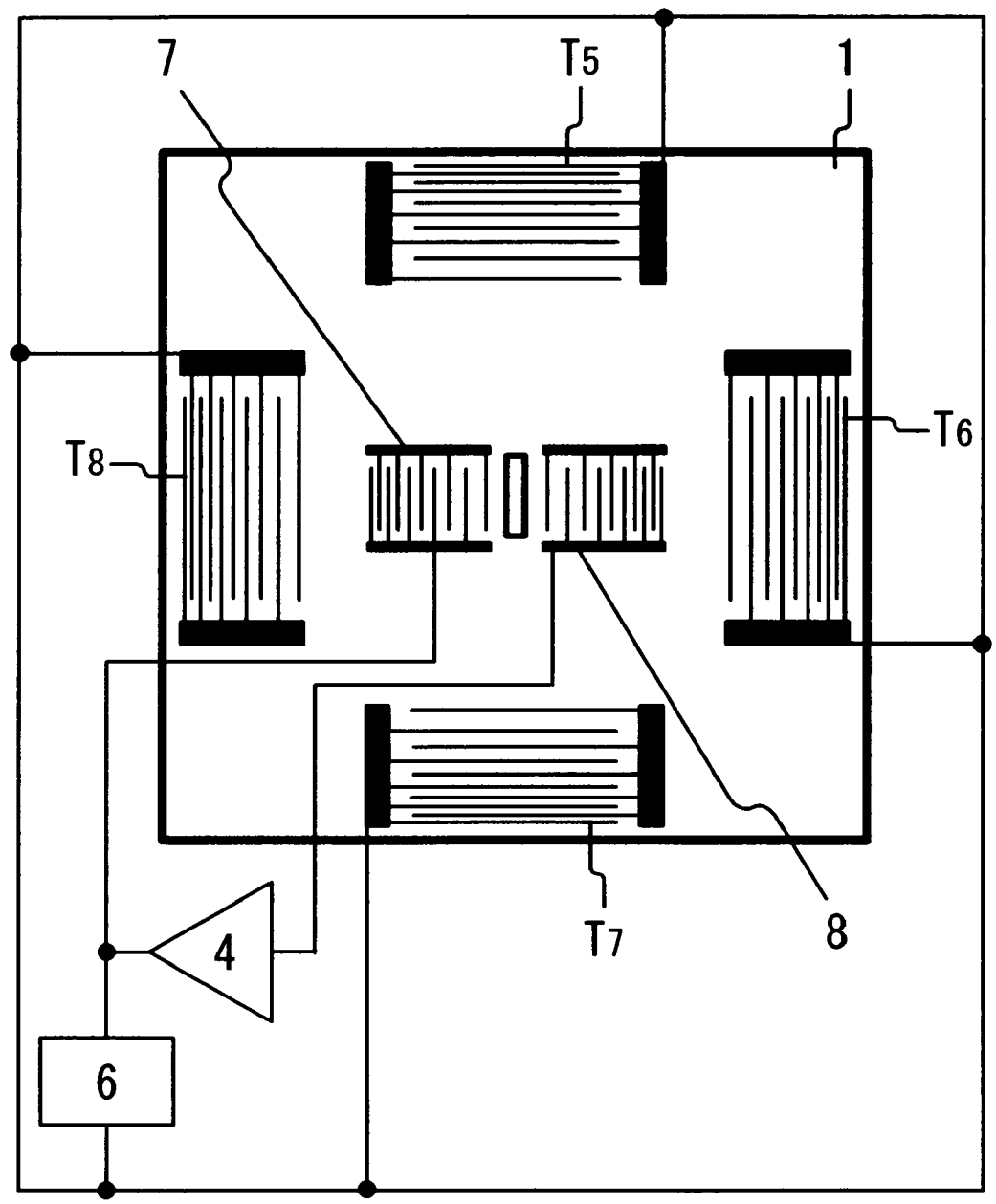
FIG. 7 shows a top plan view of an ultrasound radiation device into a material according to a third embodiment of the present invention.

FIG. 7 shows a top plan view of an ultrasound radiation device into a material according to a third embodiment of the present invention. The ultrasound radiation device into a material has the same construction as FIG. 1, except for the presence of modulator 6, the presence of input interdigital transducer 7 and output interdigital transducer 8 in place of input interdigital transducer 2 and output interdigital transducer 3, respectively, and the presence of four interdigital transducers ($T_5$, $T_6$, $T_7$ and $T_8$) in place of interdigital transducers ($T_1$, $T_2$, $T_3$ and $T_4$), respectively. Input interdigital transducer 7, output interdigital transducer 8, and interdigital transducers (Ts, $T_6$, $T_7$ and $T_8$) have combination patterns, respectively, of which each is composed of a normal interdigital electrode-pattern and a dispersive electrode-pattern having interdigital periodicities of 285-380 μm. Input interdigital transducer 7 and output interdigital transducer 8 are arranged so that the end electrode-finger participating the largest interdigital periodicity among the interdigital periodicities in input interdigital transducer 7 is close to that in output interdigital transducer 8. In other words, the dispersive electrode-pattern has the gradually increasing distance between two electrode-fingers, that is, has the longest distance between one end electrode-finger and the next electrode-finger. The end electrode-finger participating the longest distance in input interdigital transducer 7 is arranged to be close to that in output interdigital transducer 8.

In the ultrasound radiation device into a material in FIG. 7, it is possible to supply input interdigital transducer 7 with input electric signals having a wide frequency band, because of the dispersive electrode-pattern of input interdigital transducer 7. The frequency band of the input electric signals applied to input interdigital transducer 7 is still wider than that applied to input interdigital transducer 2, so that the variety of radiation-angles of the longitudinal waves from input interdigital transducer 7 is also more than that from input interdigital transducer 2.

Figure 8:
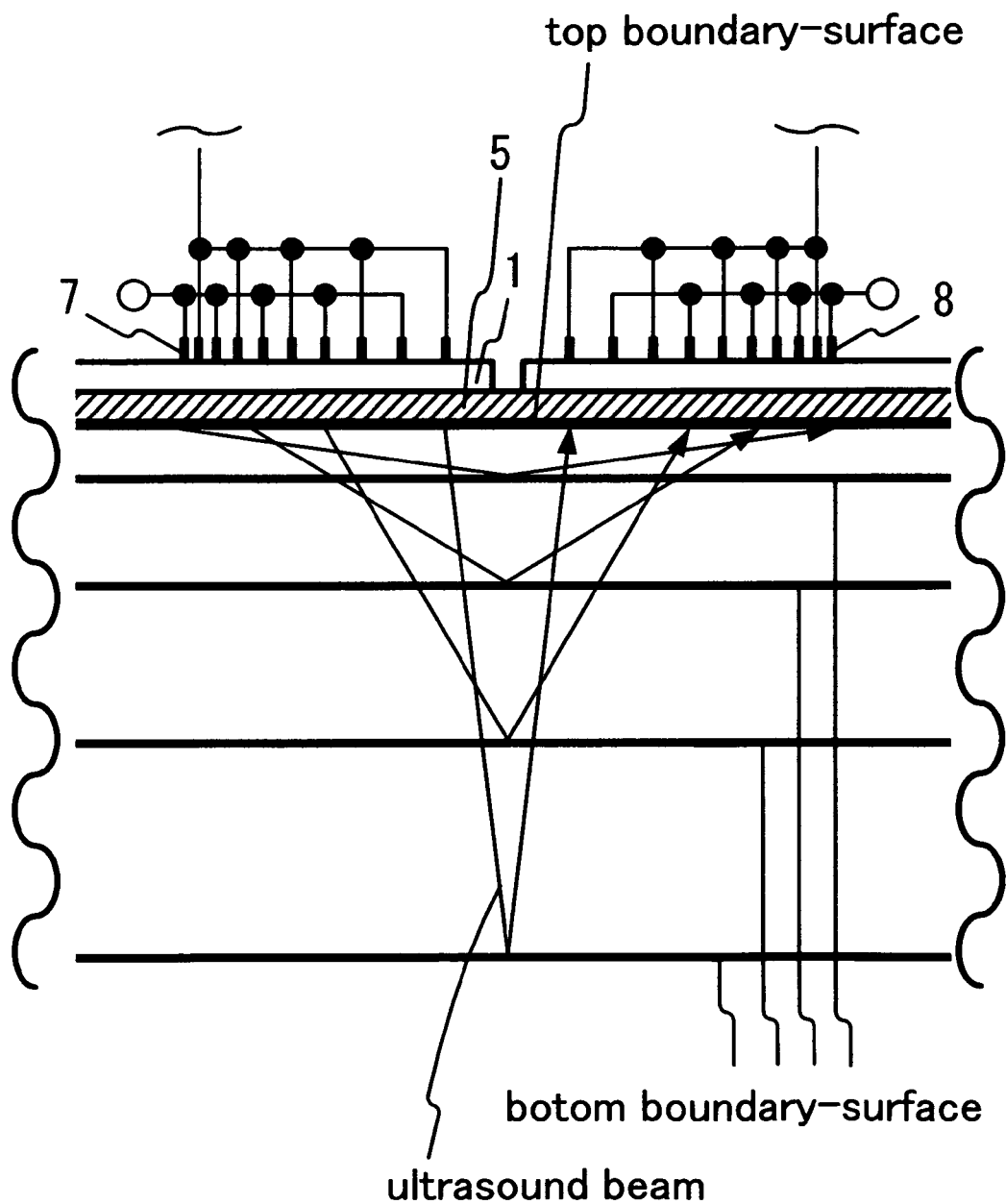
FIG. 8 shows a fragmentary sectional view of the ultrasound radiation device into a material in FIG. 7.

FIG. 8 shows a fragmentary sectional view of the ultrasound radiation device into a material in FIG. 7. Four arrows are illustrative of ultrasound beams in response to four bottom boundary-surfaces, respectively. In the same way as FIG. 5, one reflected longitudinal wave at the corresponding bottom boundary-surface is always detected as a delayed output signal at output interdigital transducer 8. However, the variety of radiation angles of the longitudinal waves is more than that in FIG. 5. The use of the dispersive electrode-pattern enables a wide variety of radiation-angles of the longitudinal waves from input interdigital transducer 7. In addition, the arrangement that the end electrode-finger participating the largest interdigital periodicity in input interdigital transducer 7 is close to that in output interdigital transducer 8 enables a wide variety of reflected longitudinal waves detected at output interdigital transducer 8.

In the ultrasound radiation device into a material in FIG. 7, the delayed output signal detected at output interdigital transducer 8 is amplified via amplifier 4. A signal part of an amplified electric signal via amplifier 4 is fed back to input interdigital transducer 7 as an input electric signal, again. Thus, input interdigital transducer 7, output interdigital transducer 8, and amplifier 4 form a self-oscillation type of delay-line oscillator. On the other hand, a remaining signal part of the amplified electric signal via amplifier 4 is transmitted to modulator 6 as a carrier signal. If an input message-signal enabling hearing by human ears is applied to modulator 6, an amplitude of the carrier signal is modulated according to the input message-signal, so that an amplitude modulated (AM) signal is generated. Thus, the AM signal is applied to interdigital transducers ($T_5$, $T_6$, $T_7$ and $T_8$), and four elastic waves are excited in piezoelectric substrate 1. The leaky component of each of the four elastic waves is radiated effectively in the form of a longitudinal wave into the material. The longitudinal wave is reflected at the bottom boundary-surface, and then re-reflected at the top boundary-surface, and thus, a continuous reflection as a chain reaction occurs. In this way, the ultrasound radiation device into a material in FIG. 7 makes the input message-signal pass efficiently through a material, for example, a liquid with a plant.

Figure 9:
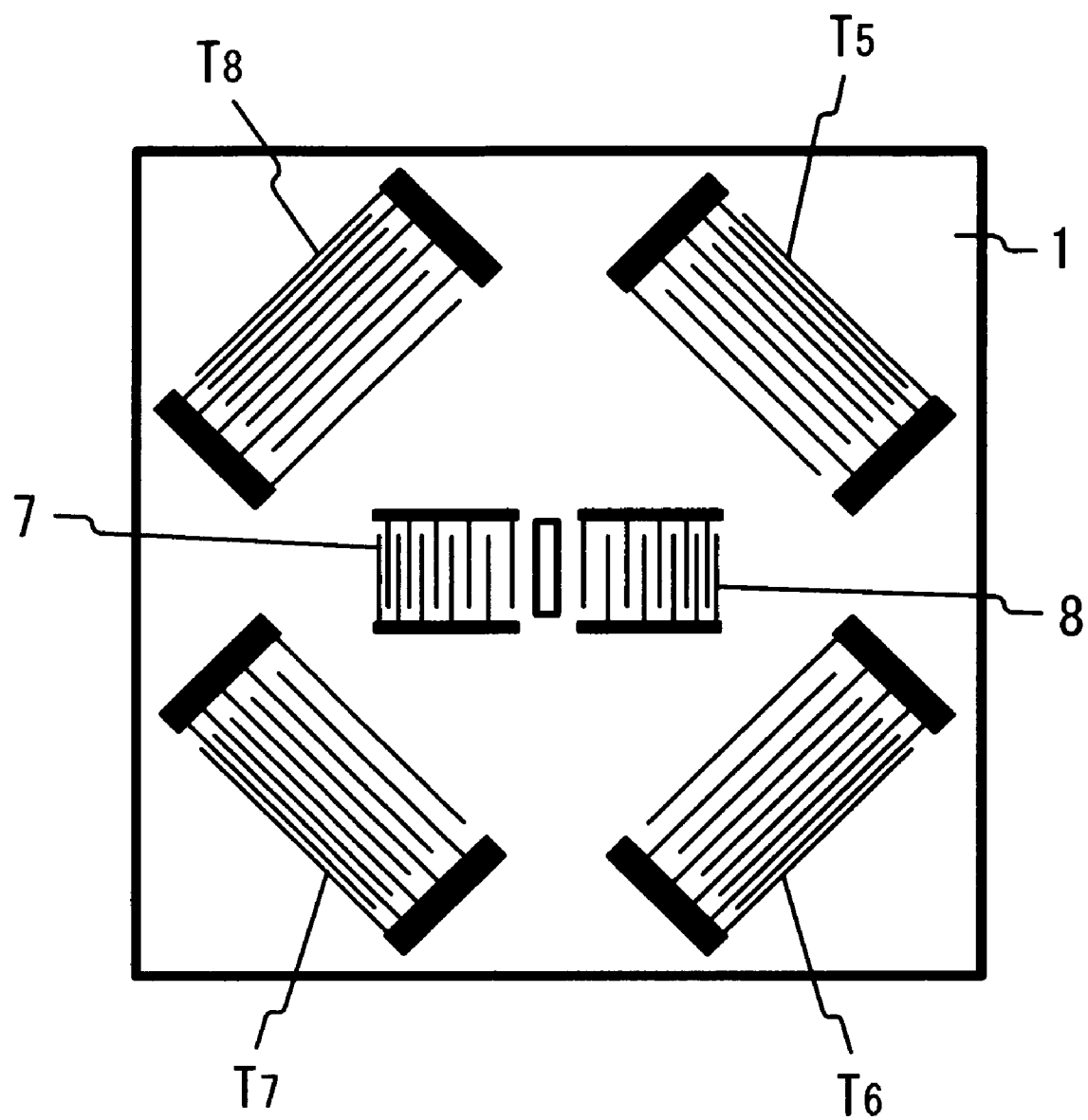
FIG. 9 shows a top plan view of an ultrasound radiation device into a material according to a fourth embodiment of the present invention.

FIG. 9 shows a top plan view of an ultrasound radiation device into a material according to a fourth embodiment of the present invention. The ultrasound radiation device into a material has the same construction as FIG. 7, except for the location of interdigital transducers ($T_5$, $T_6$, $T_7$ and $T_8$). In the same way as FIG. 6, the electrode-finger directions of interdigital transducers ($T_5$, $T_6$, $T_7$ and $T_8$) are oblique to those of input interdigital transducer 7 and output interdigital transducer 8. Interdigital transducers ($T_5$, $T_6$, $T_7$ and $T_8$) are mutually balanced for the center of the upward surface. After all, a noiseless and clear delayed output signal is detected at output interdigital transducer 8 in FIG. 9 in comparison with the ultrasound radiation device into a material in FIG. 7.

Figure 10:
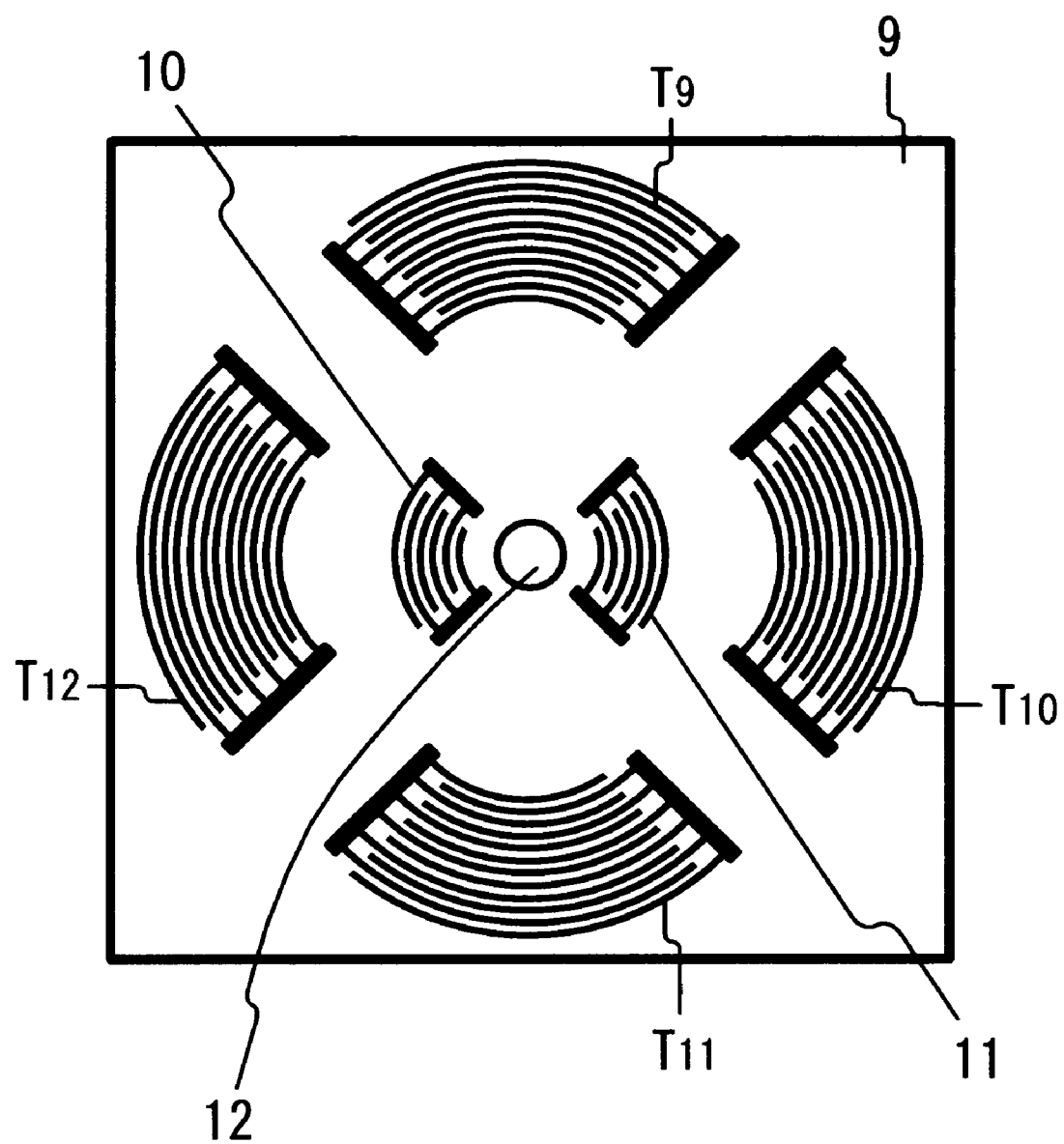
FIG. 10 shows a top plan view of an ultrasound radiation device into a material according to a fifth embodiment of the present invention.

FIG. 10 shows a top plan view of an ultrasound radiation device into a material according to a fifth embodiment of the present invention. The ultrasound radiation device into a material has the same construction as FIG. 1, except for the presence of piezoelectric substrate 9 in place of piezoelectric substrate 1, the presence of input interdigital transducer 10 and output interdigital transducer 11 in place of input interdigital transducer 2 and output interdigital transducer 3, respectively, and the presence of four interdigital transducers ($T_9$, $T_{10}$, $T_{11}$ and $T_{12}$) in place of interdigital transducers ($T_1$, $T_2$, $T_3$ and $T_4$), respectively. Piezoelectric substrate 9 has intercepting material 12 made of conductive paint between input interdigital transducer 10 and output interdigital transducer 11. Input interdigital transducer 10, output interdigital transducer 11, and interdigital transducers ($T_9$, $T_{10}$, $T_{11}$ and $T_{12}$) have arch-shaped electrode-patterns made of aluminum thin films, respectively. The arch-shaped electrode-patterns have an aperture angle of 90° and an interdigital periodicity of 340 μm, respectively. Interdigital transducers ($T_9$, $T_{10}$, $T_{11}$ and $T_{12}$) are arranged so that the apertures thereof are faced to the center of the upward surface of piezoelectric substrate 9. In this way, interdigital transducers ($T_9$, $T_{10}$, $T_{11}$ and $T_{12}$) are mutually balanced for the center of the upward surface.

In the ultrasound radiation device into a material in FIG. 10, intercepting material 12 plays the role to intercept a transmission of non-leaky components of elastic waves, which are excited in piezoelectric substrate 9 by supplying input interdigital transducer 10 with input electric signals $E_i$ with frequencies $f_i$, respectively. The ultrasound radiation device into a material in FIG. 10 fulfills the same function as that in FIG. 1, except that the radiation directions of the longitudinal waves from input interdigital transducer 10 and interdigital transducers ($T_9$, $T_{10}$, $T_{11}$ and $T_{12}$) are different from those from input interdigital transducer 2 and interdigital transducers ($T_1$, $T_2$, $T_3$ and $T_4$) in FIG. 1.

Figure 11:
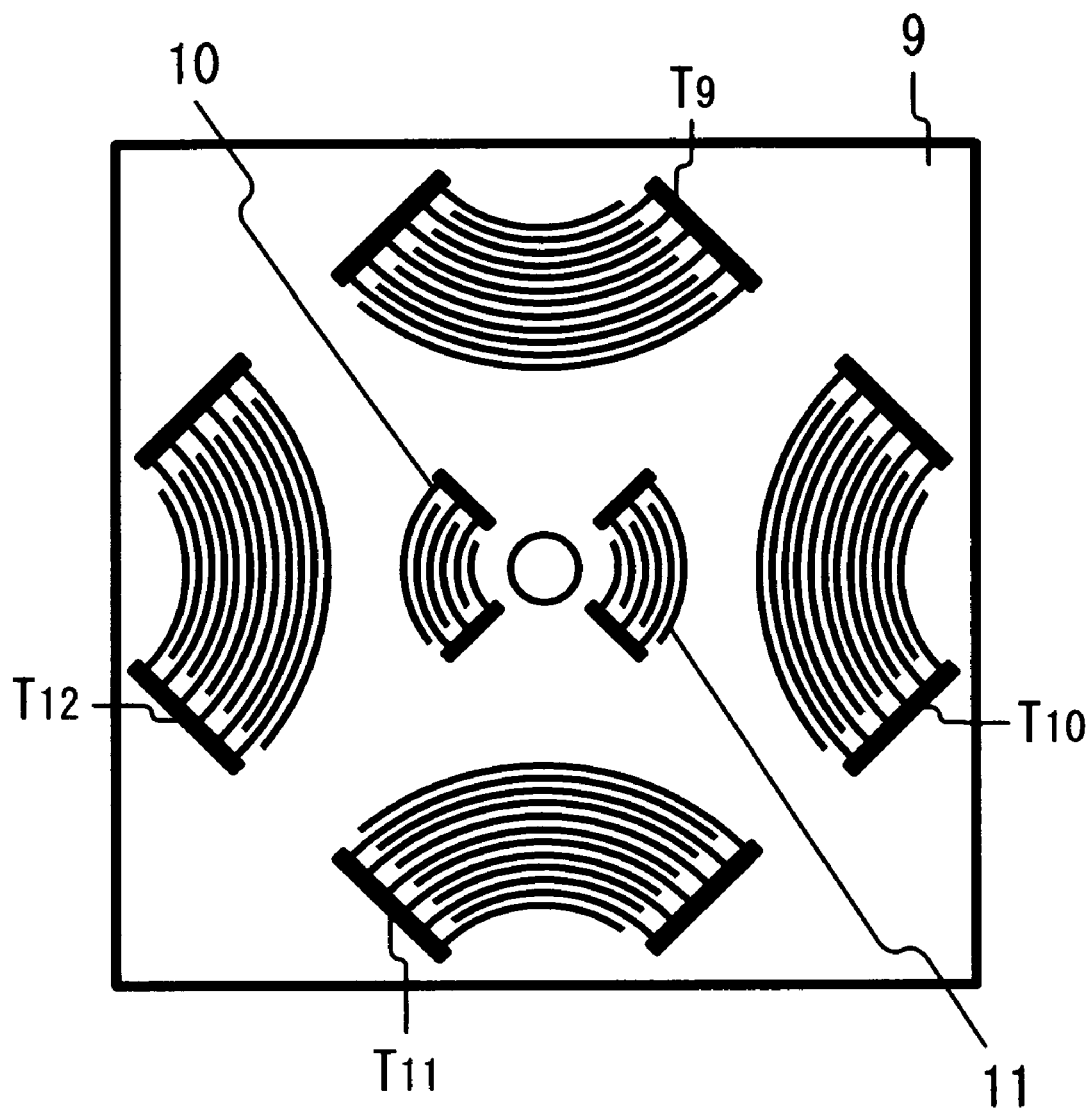
FIG. 11 shows a top plan view of an ultrasound radiation device into a material according to a sixth embodiment of the present invention.

FIG. 11 shows a top plan view of an ultrasound radiation device into a material according to a sixth embodiment of the present invention. The ultrasound radiation device into a material has the same construction as FIG. 10, except for the location of interdigital transducers ($T_9$, $T_{10}$, $T_{11}$ and $T_{12}$), which are arranged so that the apertures thereof are faced with their backs to the center of the upward surface of piezoelectric substrate 9. Thus, interdigital transducers ($T_9$, $T_{10}$, $T_{11}$ and $T_{12}$) are mutually balanced for the center of the upward surface. The ultrasound radiation device into a material in FIG. 11 fulfills the same function as that in FIG. 10, except that the radiation directions of the longitudinal waves from interdigital transducers ($T_9$, $T_{10}$, $T_{11}$ and $T_{12}$) are different from FIG. 10.

Figure 12:
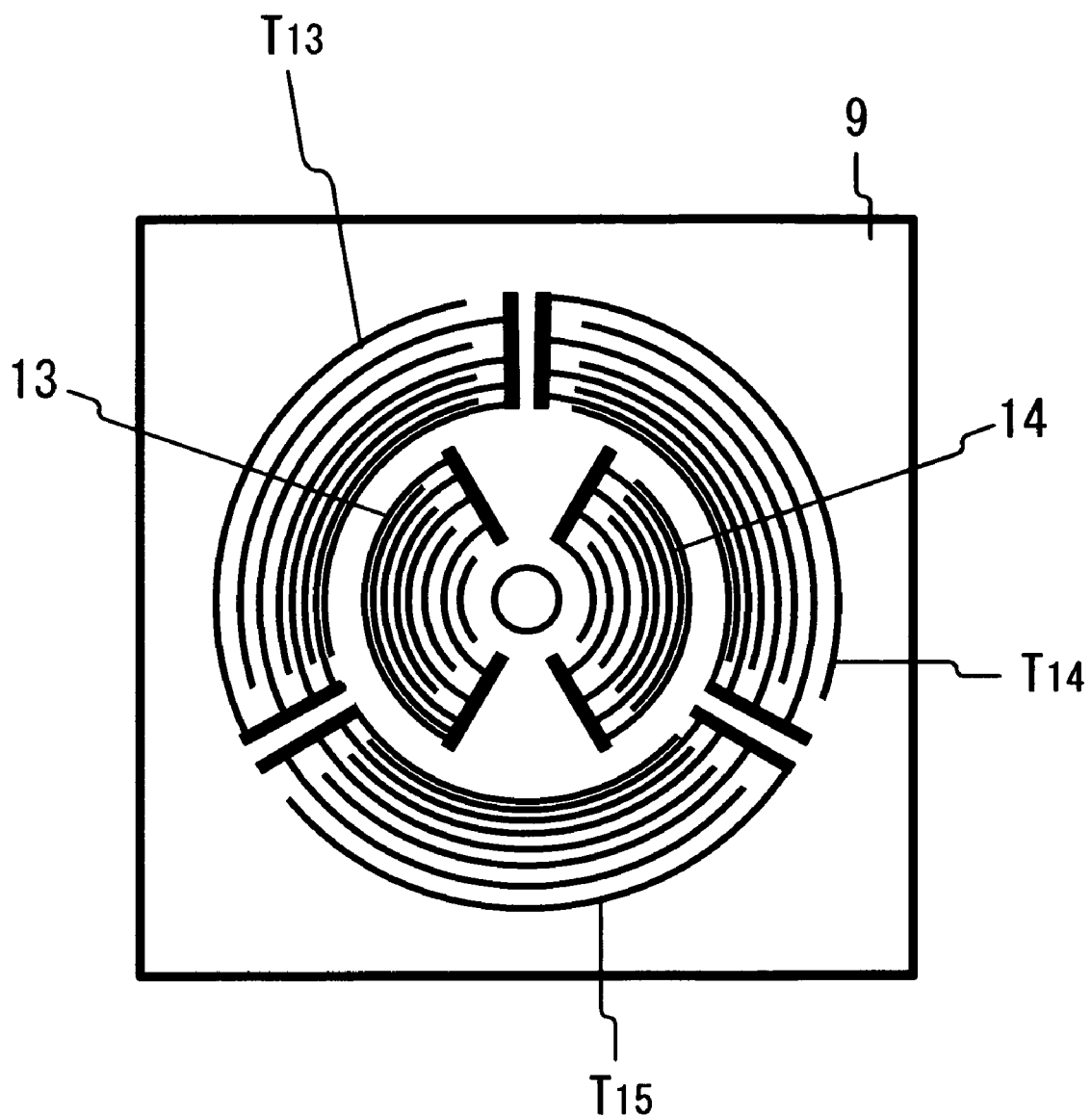
FIG. 12 shows a top plan view of an ultrasound radiation device into a material according to a seventh embodiment of the present invention.

FIG. 12 shows a top plan view of an ultrasound radiation device into a material according to a seventh embodiment of the present invention. The ultrasound radiation device into a material has the same construction as FIG. 10, except for the presence of input interdigital transducer 13 and output interdigital transducer 14 in place of input interdigital transducer 10 and output interdigital transducer 11, respectively, the presence of interdigital transducers ($T_{13}$, $T_{14}$ and $T_{15}$), and the absence of interdigital transducers ($T_9$, $T_{10}$, $T_{11}$ and $T_{12}$). Input interdigital transducer 13, output interdigital transducer 14 and interdigital transducers ($T_{13}$, $T_{14}$ and $T_{15}$) have combination patterns, respectively, of which each is composed of an arch-shaped electrode-pattern having an aperture angle of 120° and a dispersive electrode-pattern having interdigital periodicities of 285-380 μm. Input interdigital transducer 13 and output interdigital transducer 14 are arranged so that the end electrode-finger participating the largest interdigital periodicity among the interdigital periodicities in input interdigital transducer 13 is close to that in output interdigital transducer 14. In other words, the dispersive electrode-pattern has the gradually increasing distance between two electrode-fingers, that is, has the longest distance between one end electrode-finger and the next electrode-finger. The end electrode-finger participating the longest distance in input interdigital transducer 13 is arranged to be close to that in output interdigital transducer 14. The ultrasound radiation device into a material in FIG. 12 fulfills the same function as that in FIG. 7, except that the radiation directions of the longitudinal waves from input interdigital transducer 13 and interdigital transducers ($T_{13}$, $T_{14}$ and $T_{15}$) are different from those from input interdigital transducer 7 and interdigital transducers ($T_5$, $T_6$, $T_7$ and $T_8$) in FIG. 7.

Figure 13:
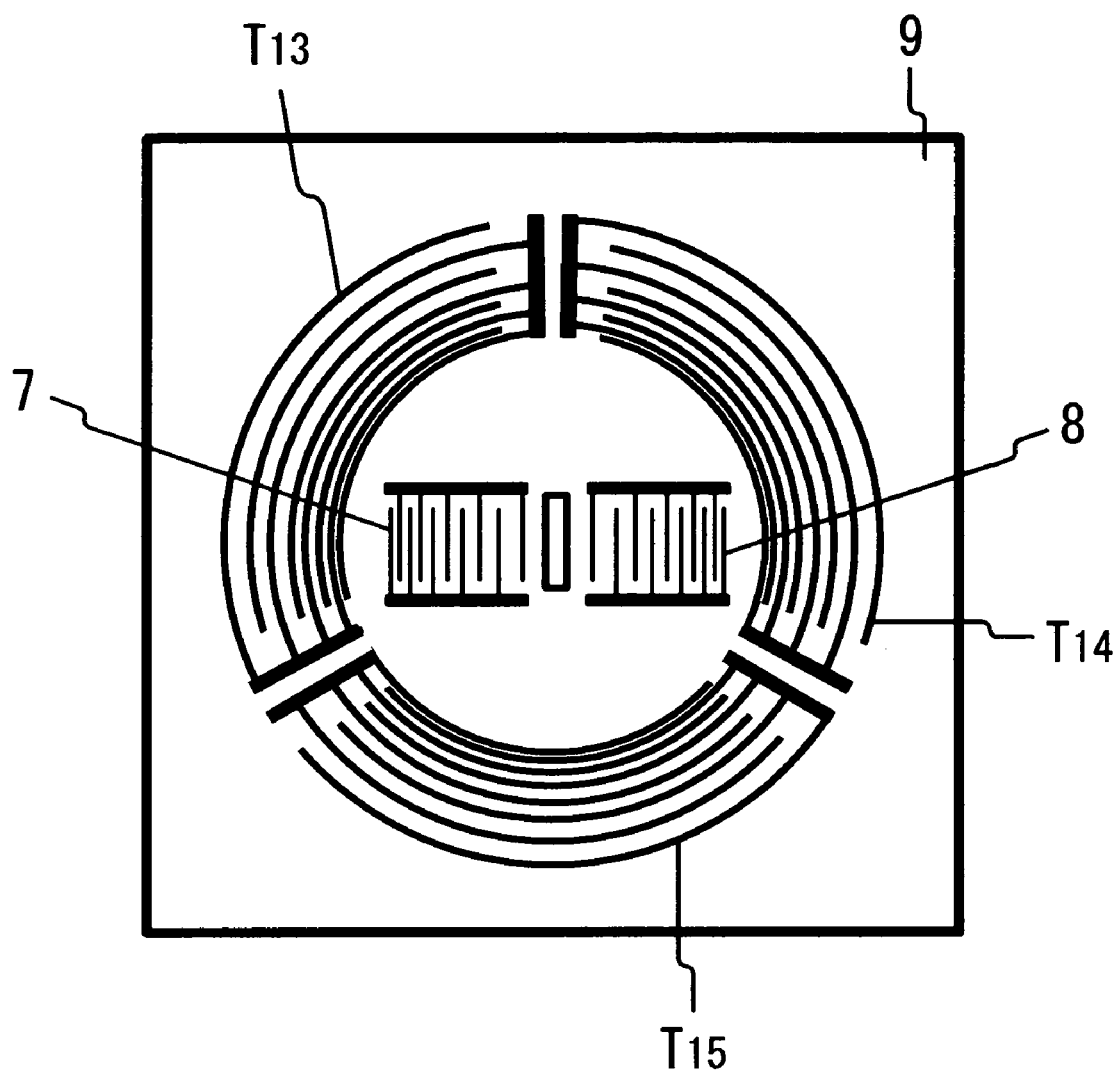
FIG. 13 shows a top plan view of an ultrasound radiation device into a material according to an eighth embodiment of the present invention.

FIG. 13 shows a top plan view of an ultrasound radiation device into a material according to an eighth embodiment of the present invention. The ultrasound radiation device into a material has the same construction as FIG. 12, except for the presence of input interdigital transducer 7 and output interdigital transducer 8 in place of input interdigital transducer 13 and output interdigital transducer 14, respectively. The ultrasound radiation device into a material in FIG. 13 fulfills the same function as that in FIG. 12, except that the radiation directions of the longitudinal waves from input interdigital transducer 7 are the same as FIG. 7.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope the appended claims.

What is claimed is:

1. An ultrasound radiation device into a material comprising:
   a piezoelectric substrate;
   an input interdigital transducer formed on a central surface-part of an upward surface of said piezoelectric substrate;
   an output interdigital transducer located beside said input interdigital transducer on said central surface-part;
   another at least one interdigital transducer formed on a surrounding surface-part of said upward surface; and
   an amplifier,
   said input interdigital transducer receiving input electric signals $E_i$ (i=1, 2, ..., n) with frequencies $f_i$ (i=1, 2, ..., n), respectively, at a time, exciting elastic waves in said piezoelectric substrate, radiating leaky components of said elastic waves in the form of longitudinal waves into a material, and making a bottom boundary-surface of said material reflect said longitudinal waves back,
   said output interdigital transducer detecting one of reflected longitudinal waves at said bottom boundary-surface as a delayed output signal, which has one of said frequencies $f_i$ in accordance with a distance between said bottom boundary-surface and a top boundary-surface of said material,
   said amplifier amplifying said delayed output signal and feeding a signal part of an amplified electric signal back to said input interdigital transducer, again, and thus causing a self-oscillation type of delay-line oscillator operating at said one of said frequencies $f_i$,
   said another at least one interdigital transducer receiving a remaining signal part of said amplified electric signal, exciting an elastic wave in said piezoelectric substrate, radiating a leaky component of said elastic wave in the form of a longitudinal wave into said material, making said longitudinal wave reflect at said bottom boundary-surface and re-reflect at said top boundary-surface of said material, and thus causing a continuous reflection as a chain reaction.

2. An ultrasound radiation device into a material as defined in claim 1 further comprising a polymer film, with which a downward surface of said piezoelectric substrate is coated.

3. An ultrasound radiation device into a material as defined in claim 1, wherein said piezoelectric substrate has a hole between said input- and output interdigital transducers on said central surface-part.

4. An ultrasound radiation device into a material as defined in claim 1, wherein said piezoelectric substrate has an intercepting material between said input- and output interdigital transducers on said central surface-part.

5. An ultrasound radiation device into a material as defined in claim 1, wherein said piezoelectric substrate has an intercepting material, with conductivity, between said input- and output interdigital transducers on said central surface-part.

6. An ultrasound radiation device into a material as defined in claim 1, wherein said piezoelectric substrate is made of a piezoelectric ceramic thin plate, the polarization axis thereof being parallel to the thickness direction thereof.

7. An ultrasound radiation device into a material as defined in claim 1, wherein said piezoelectric substrate is made of a piezoelectric polymer thin film.

8. An ultrasound radiation device into a material as defined in claim 1, wherein said input- and output interdigital transducers have normal interdigital electrode-patterns, respectively.

9. An ultrasound radiation device into a material as defined in claim 1, wherein said another at least one interdigital transducer has normal interdigital electrode-pattern.

10. An ultrasound radiation device into a material as defined in claim 1, wherein said input- and output interdigital transducers and said another at least one interdigital transducer have normal interdigital electrode-patterns, respectively, and the electrode-finger length of said another at least one interdigital transducer is longer than the electrode-finger lengths of said input- and output interdigital transducers.

11. An ultrasound radiation device into a material as defined in claim 1, wherein said input- and output interdigital transducers and said another at least one interdigital transducer have normal interdigital electrode-patterns, respectively, and the electrode-finger direction of said another at least one interdigital transducer is oblique to the electrode-finger directions of said input- and output interdigital transducers.

12. An ultrasound radiation device into a material as defined in claim 1, wherein said input- and output interdigital transducers have arch-shaped electrode-patterns, respectively.

13. An ultrasound radiation device into a material as defined in claim 1, wherein said another at least one interdigital transducer has an arch-shaped electrode-pattern.

14. An ultrasound radiation device into a material as defined in claim 1, wherein said another at least one interdigital transducer has an arch-shaped electrode-pattern, and is arranged so that the aperture thereof is faced to the center of said upward surface.

15. An ultrasound radiation device into a material as defined in claim 1, wherein said another at least one interdigital transducer has an arch-shaped electrode-pattern, and is arranged so that the aperture thereof is faced with its back to the center of said upward surface.

16. An ultrasound radiation device into a material as defined in claim 1, wherein said input- and output interdigital transducers and said another at least one interdigital transducer have dispersive electrode-patterns, respectively, of which each has a series of interdigital periodicities.

17. An ultrasound radiation device into a material as defined in claim 1, wherein said input- and output interdigital transducers and said another at least one interdigital transducer have dispersive electrode-patterns, respectively, of which each has a series of interdigital periodicities, and
said input- and output interdigital transducers are arranged so that one end electrode-finger participating the largest interdigital periodicity among said interdigital periodicities in said input interdigital transducer is close to that in said output interdigital transducer.

18. An ultrasound radiation device into a material as defined in claim 1 further comprising a modulator which receives not only an input message-signal but also said remaining signal part as a carrier signal, modulates an amplitude of said carrier signal according to said input message-signal, and generates an amplitude-modulated signal, and then makes said another at least one interdigital transducer receive said amplitude-modulated signal.

19. An ultrasound radiation device into a material comprising:
a piezoelectric substrate;
an input interdigital transducer formed on a central surface-part of an upward surface of said piezoelectric substrate;
an output interdigital transducer located beside said input interdigital transducer on said central surface-part;
another at least two interdigital transducers formed on a surrounding surface-part of said upward surface such that said another at least two interdigital transducers are mutually balanced for the center of said upward surface; and
an amplifier,
said input interdigital transducer receiving input electric signals $E_i$ (i=1, 2, ..., n) with frequencies $f_i$ (i=1, 2, ..., n), respectively, at a time, exciting elastic waves in said piezoelectric substrate, radiating leaky components of said elastic waves in the form of longitudinal waves into a material, and making a bottom boundary-surface of said material reflect said longitudinal waves back,
said output interdigital transducer detecting one of reflected longitudinal waves at said bottom boundary-surface as a delayed output signal, which has one of said frequencies $f_i$ in accordance with a distance between said bottom boundary-surface and a top boundary-surface of said material,
said amplifier amplifying said delayed output signal and feeding a signal part of an amplified electric signal back to said input interdigital transducer, again, and thus causing a self-oscillation type of delay-line oscillator operating at said one of said frequencies $f_i$,
each of said another at least two interdigital transducers receiving a remaining signal part of said amplified electric signal, exciting an elastic wave in said piezoelectric substrate, radiating a leaky component of said elastic wave in the form of a longitudinal wave into said material, making said longitudinal wave reflect at said bottom boundary-surface and re-reflect at said top boundary-surface of said material, and thus causing a continuous reflection as a chain reaction.

* * * * *